(12) United States Patent
Chowdhury et al.

(10) Patent No.: US 7,908,729 B2
(45) Date of Patent: Mar. 22, 2011

(54) METHOD FOR MAKING A LOLLIPOP (75) Inventors: Tahseen A. Chowdhury, Washington Township, NJ (US); Edward J. Gabrielski, Bound Brook, NJ (US); Christopher H. Baker, Forest, VA (US)

(73) Assignee: Teva Women's Health, Inc., Woodcliff Lake, NJ (US)

( * ) Notice: Subject to any disclaimer, the term of this patent is extended or adjusted under 35 U.S.C. 154(b) by 1131 days.

(21) Appl. No.: 11/556,378

(22) Filed: Nov. 3, 2006

(65) Prior Publication Data

US 2007/0107200 A1    May 17, 2007

Related U.S. Application Data

(63) Continuation-in-part of application No. 11/446,510, filed on Jun. 5, 2006.

(60) Provisional application No. 60/686,976, filed on Jun. 3, 2005.

(51) Int. Cl.
*B21D 39/03* (2006.01)
*B23P 11/00* (2006.01)

(52) U.S. Cl. ............ 29/428; 29/429; 29/430; 29/525.13

(58) Field of Classification Search ............ 29/428–430, 29/432.1, 445, 525.13, 799; 425/116, 126.2, 425/174.2, 305.1, 468
See application file for complete search history.

(56) References Cited

U.S. PATENT DOCUMENTS 2,637,281 A * 5/1953 Latini et al. ................. 425/116
3,557,267 A   1/1971 Angelotti et al.
3,972,758 A   8/1976 Bieber
4,478,822 A   10/1984 Haslam et al.
4,548,771 A   10/1985 Senapati et al.
4,671,953 A   6/1987 Stanley et al.
4,885,173 A   12/1989 Stanley et al.
(Continued)

FOREIGN PATENT DOCUMENTS

GB       636 219 A          4/1950
JP    2003 320496 A         11/2003
WO   WO 2006/100274 A        9/2006

OTHER PUBLICATIONS

International Search Report for International Application No. PCT/US2007/022428, mailed Jun. 2, 2008, 4 pgs.

(Continued)

*Primary Examiner* — Thiem Phan
(74) *Attorney, Agent, or Firm* — Sterne, Kessler, Goldstein & Fox P.L.L.C.

(57) ABSTRACT

A method for attaching a handle to a tablet to form a lollipop utilizes a specific work holder. The work holder has a tooling pallet with a plurality of openings going from a top surface to a bottom surface. A bullet and a spring are located in each opening and held in place by a plate that slides through a groove in the bottom surface of the tooling pallet to block the openings in the bottom surface. Each spring is positioned between a bullet and the plate. A tablet is placed in a cavity of each bullet and a handle is placed in contact with each tablet. High frequency mechanical vibrations, such as ultrasonic vibrations, are applied to a joint interface between each tablet and bullet until the joint interface reaches a molten state. The joint interfaces are then allowed to cool, thereby attaching a handle to each tablet and forming a lollipop.

19 Claims, 4 Drawing Sheets

U.S. PATENT DOCUMENTS

| | | | |
|---|---|---|---|
| 5,132,114 A | | 7/1992 | Stanley et al. |
| 5,211,892 A | * | 5/1993 | Gueret .......................... 264/443 |
| 5,298,256 A | | 3/1994 | Flockhart et al. |
| 5,711,961 A | | 1/1998 | Reiner et al. |
| 6,019,154 A | | 2/2000 | Ma et al. |
| 6,077,144 A | | 6/2000 | Fishman |
| 6,802,920 B2 | | 10/2004 | Shinohara et al. |
| 2004/0213828 A1 | * | 10/2004 | Smith .......................... 424/440 |

OTHER PUBLICATIONS

Written Opinion of the International Searching Authority for International Application No. PCT/US2007/022428, mailed Jun. 2, 2008, 7 pgs.

"Application Technology," webpage available at http://www.staplaultrasonics.com/c6-app/app.htm, STAPLA Ultrasonics Corporation, STAPLA Ultrasonics Corporation, 3 pages (accessed Aug. 2004).

"Introduction: A broad field of applications," webpage available at http://www.staplaultrasonics.com/intro/intro.htm, STAPLA Ultrasonics Corporation, STAPLA Ultrasonics Corporation, 2 pages (accessed Aug. 2004).

"Ultrasonic Systems," http://www.branson-plasticsjoin.com/ultrasonic.html, Branson Ultrasonics Corporation, Branson Ultrasonics Corporation, 6 pages (accessed Aug. 2004).

* cited by examiner

METHOD FOR MAKING A LOLLIPOP

CROSS REFERENCE TO RELATED APPLICATIONS

This application is a continuation-in-part of U.S. patent application Ser. No. 11/446,510, filed on Jun. 5, 2006, which claims the benefit of the filing date of U.S. patent application Ser. No. 60/686,976, filed Jun. 3, 2005, both of which are hereby incorporated by reference in their entirety.

BACKGROUND OF THE INVENTION

1. Field of the Invention

The present invention relates to a work holder for attaching a handle to a tablet, such as a solid oral dosage form to form a lollipop and to a method for making the same utilizing the work holder.

2. Background Art

A conventional solid oral dosage form of a pharmaceutical attached to a handle for transmucosal active agent delivery is disclosed in U.S. Pat. No. 4,671,953. In addition to being non-invasive and providing a particularly easy method of delivery, the solid oral dosage form attached to a handle allows a patient or caregiver to move the dose in and out of the mouth to titrate the dose. This practice is called dose-to-effect, in which a patient or caregiver controls the administration of the dose until the expected therapeutic effect is achieved. The practice of dose-to-effect is particularly important for certain symptoms, such as pain, nausea, motion sickness, and premedication prior to anesthesia because each patient needs a different amount of medication to treat these symptoms. Once the appropriate amount of active agent is delivered, the patient or caregiver can remove the solid oral dosage form, thus stopping the active agent delivery to prevent overdose.

A common concern with medicated solid oral dosage forms attached to a handle is the possibility that the solid oral dosage form part of the device will become detached from the handle. If the solid oral dosage form becomes detached from the handle, then it can be more difficult to remove and/or administer the active agent as desired. Also of concern is the possibility that the solid oral dosage form which is detached from its handle could be swallowed in its entirety, possibly resulting in an overdosing of the active agent. Similarly, a detached solid oral dosage form could also become a choking hazard.

One method for securely attaching a solid oral dosage form to a handle is the use of mechanical vibrations, such as ultrasonic vibrations, as disclosed in parent application U.S. patent application Ser. No. 11/446,510, filed on Jun. 5, 2006. Such a process involves having the handle inserted into a solid oral dosage form and exerting pressure on the handle with a horn to transmit the vibrations. One problem with attaching several handles and solid oral dosage forms together with the same horn in an automated process is that if the handles are not at the same height, either some handles will not be attached or too much pressure will be applied to some handles resulting in cracking of the solid oral dosage forms.

Therefore, there is a need in the art for a work holder that can hold the tablet portion of a lollipop such as, for example, solid oral dosage forms with the handles inserted therein during an attachment procedure that permits relative movement of the individually assembled handles and tablets. Such a work holder that allows relative movement ensures attachment of all the handles to the tablets and prevents the exertion of too much pressure on some handles, which leads to cracking of the tablets.

BRIEF SUMMARY OF THE INVENTION

A work holder according to one embodiment of the present invention comprises a tooling pallet having a first surface, a second surface, and a plurality of openings in the first surface; a plurality of bullets, wherein each bullet has a first cavity and wherein each of the plurality of bullets is inserted into one of the plurality of openings in the tooling pallet; and a plurality of springs, wherein each of the plurality of springs is located in one of the plurality of openings in the tooling pallet between one of the plurality of bullets and a surface.

A work holder according to another embodiment of the present invention is for use in ultrasonically bonding a handle to a solid oral dosage form. The work holder comprises a tooling pallet having a first surface, a second surface, a plurality of openings extending through the tooling pallet from the first surface to the second surface and a groove extending along a length of the second surface of the tooling pallet; a plate inserted in the groove of the tooling pallet and blocking the plurality of openings in the second surface of the tooling pallet; a plurality of bullets, wherein each of the plurality bullets has a first cavity shaped to receive a solid oral dosage on one side and a second cavity shaped to receive a spring on another side and wherein each of the plurality of bullets is inserted into one of the plurality of openings in the tooling pallet such that the first cavity faces a first surface of the tooling pallet and the second cavity faces the plate; and a plurality of springs, wherein each spring fits in one of the second and wherein each spring is located between one of the plurality of bullets and the plate.

Another embodiment of the present invention relates to a method for attaching a handle to a tablet to form a lollipop. The method comprises providing a work holder comprising a tooling pallet having a first surface, a second surface, and a plurality of openings in the first surface; a plurality of bullets, wherein each bullet has a first cavity in and wherein each of the plurality of bullets is inserted into one of the plurality of openings in the tooling pallet; and a plurality of springs, wherein each of the plurality of springs is located in one of the plurality of openings in the tooling pallet between one of the plurality of bullets and a surface. A tablet is placed in each of the first cavities of the plurality of bullets and then a handle is placed in contact with each tablet, wherein an area of contact between each handle and each tablet forms a joint interface. High frequency mechanical vibrations are applied to the joint interfaces until each tablet at each joint interface reaches a molten state and the joint interfaces cooled from the molten state to allow solidification, thereby attaching a handle to each tablet to form a lollipop.

DETAILED DESCRIPTION OF THE INVENTION

The present invention relates to a work holder for attaching a handle to tablet to form a lollipop and to a method for making a lollipop utilizing the work holder.

Figure 1:
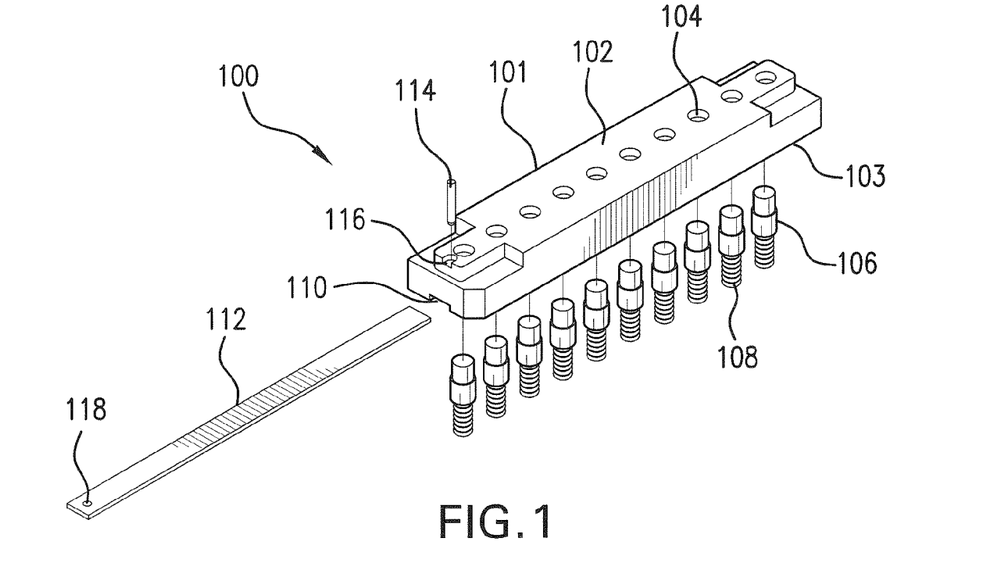
FIG. 1 is an exploded view of the work holder of the present invention.
Figure 2:
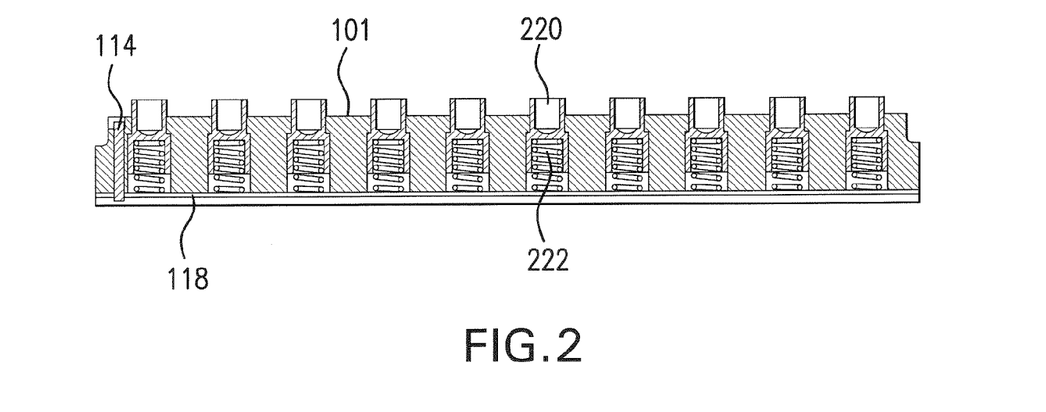
FIG. 2 is a cross sectional view along a length of the work holder.

The work holder of the present invention will now be described with reference to FIGS. 1-6. The work holder 100 includes a tooling pallet 101 having a first surface 102 and a second surface 103 and a plurality of openings 104 in first surface 102. Tooling pallet 101 is preferably made of ultra molecular weight polystyrene, although one skilled in the art would have readily appreciated other materials could be utilized including, without limitation, polymeric materials, steel or nylon. Each opening 104 houses a bullet 106 and a spring 108. Bullets 106 and springs 108 are preferably made of stainless steel. Springs 108 preferably have a spring constant in a range of about 21.2 lbs/in to about 21.8 lbs/in. In a preferred embodiment, the plurality of openings 104 extend from first surface 102 of tooling pallet 101 to second surface 103 of tooling pallet 101. Bottom surface 103 of tooling pallet 101 has a groove 110 along its length for receiving a plate 112. Plate 112 covers openings 104 in bottom surface 103 of tooling pallet 101 such that bullets 106 and springs 108 are retained in the plurality of openings 104 and plate 112 is preferably made of stainless steel. A pin 114 locks plate 112 and tooling pallet 101 together by passing through an opening 116 in tooling pallet 101 and an opening 118 in plate 112. As shown in FIG. 2, each bullet 106 has an upper cavity 220 for receiving a tablet portion of a lollipop, such as a solid oral dosage form, and handle and a lower cavity 222 for receiving a spring 108. Each bullet 106 is positioned in an opening 104 such that each spring 108 is located in lower cavity 222 between plate 112 and a bullet 106 and upper cavity 220 faces away from plate 112.

Figure 3:
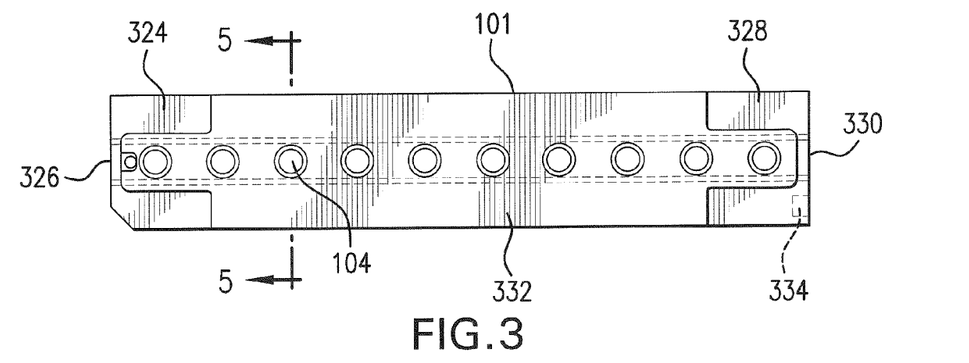
FIG. 3 is a top plan view of the work holder.
Figure 4:
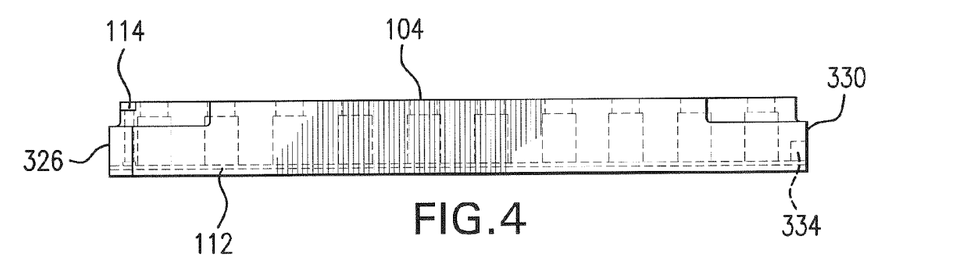
FIG. 4 is a side view of the work holder.

As shown in FIG. 3, first surface 102 of tooling pallet 101 has a first recess 324, that is preferably C-shaped at a first end 326 and a second recess 328, that is also preferably C-shaped at a second end 330 and an island 332 in between recesses 324, 328. Second end 330 also has a hole 334. In a preferred embodiment tooling pallet 101 is 15.5 inches in length, 2.95 inches in width and 1.688 inches in height. Island 332 has a length of 15.0 inches and is set back 0.25 inches from both first end 326 and second end 330 of tooling pallet 101. Preferably there are 10 openings 104 in first surface 102 of tooling pallet 101 with a spacing of 0.50 inches between the centers of adjacent openings. The centers of the first and last openings are spaced 1.0 inches from first and second ends 326, 330 of the tooling pallet 101, respectively. Pin opening 116 in first surface 102 of tooling pallet 101 is preferably 0.38 inches in diameter and located on island 332 near first end 326 and its center is preferably aligned with the centers of openings 104. Hole 334 is preferably 0.472 inches in diameter and 0.32 inches deep. Hole 334 is sized to accommodate a radio frequency identification (RFID) tag. Plate 112 is preferably 15.5 inches in length, 0.975 inches in length and 0.078 inches in thickness. Pin opening 118 in the plate 112 is preferably 0.192 inches in diameter and the center of the pin opening 118 is preferably 0.44 inches from an end of plate 112 and is positioned such that when plate 112 is in groove 110 pin opening 118 and pin opening 116 are aligned.

Figure 5:
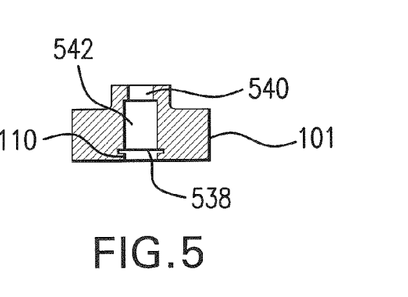
FIG. 5 is a cross sectional view taken along line 5-5 in FIG. 3.

As shown in FIG. 5, groove 110 is located directly above and is connected to opening 538, which runs along a longitudinal axis in second surface 103. Groove 110 holds plate 112 and preferably has a width of 1.0 inch and a height of 0.09 inches. Opening 538 preferably has a width of 0.79 inches and a height of 0.13 inches. Openings 104 have an upper cylindrical portion 540 and a lower cylindrical portion 542. Upper cylindrical portion 540 is adjacent first surface 102 and preferably has a diameter of approximately 0.626 inches and lower cylindrical portion 542 is adjacent second surface 103 and preferably has a diameter of approximately 0.751 inches.

Figure 6:
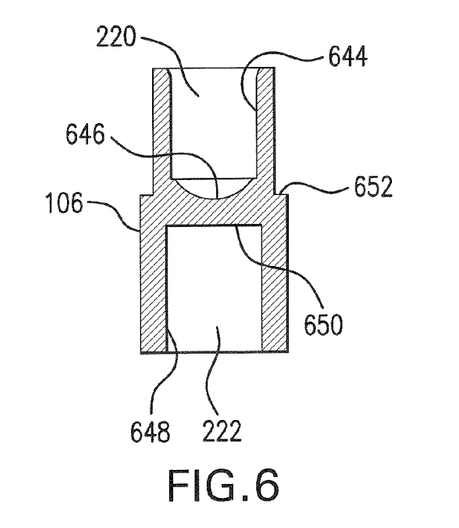
FIG. 6 is a cross sectional view of the bullet portion of the work holder.

As shown in FIG. 6, each of bullets 106 has an upper cavity 220 defined by a cylindrical wall 644 and a bottom concave surface 646 and a lower cavity 222 defined by a cylindrical wall 648 and a top flat surface 650. A ledge 652 is disposed between upper cavity 220 and the lower cavity 222. Ledge 652 of bullet 106 abuts a transition between upper cylindrical portion 540 and lower cylindrical portion 542 of opening 104 when inserted therein and requires that bullet 106 be inserted into opening 104 through bottom surface 103 with upper cavity 220 entering first. Bullet 106 preferably has a length of 1.487 inches. Upper cavity 220 preferably has an inner diameter of 0.448 inches, an outer diameter of 0.625 inches and a depth of 0.688 inches. Bottom concave surface 646 of upper cavity 220 is preferably rounded with a radius of curvature of 0.258 inches and the depth of the curve is about 0.091 inches. Lower cavity 222 preferably has an inner diameter of 0.5 inches, an outer diameter of 0.75 inches and a depth of 0.656 inches.

It is noted that all the dimensions for the various parts of work holder 100 given above, as well as the number of openings 104, are exemplary and can be varied as needed depending upon the intended application and the parameters of the materials to be held in the work holder.

Figure 7:
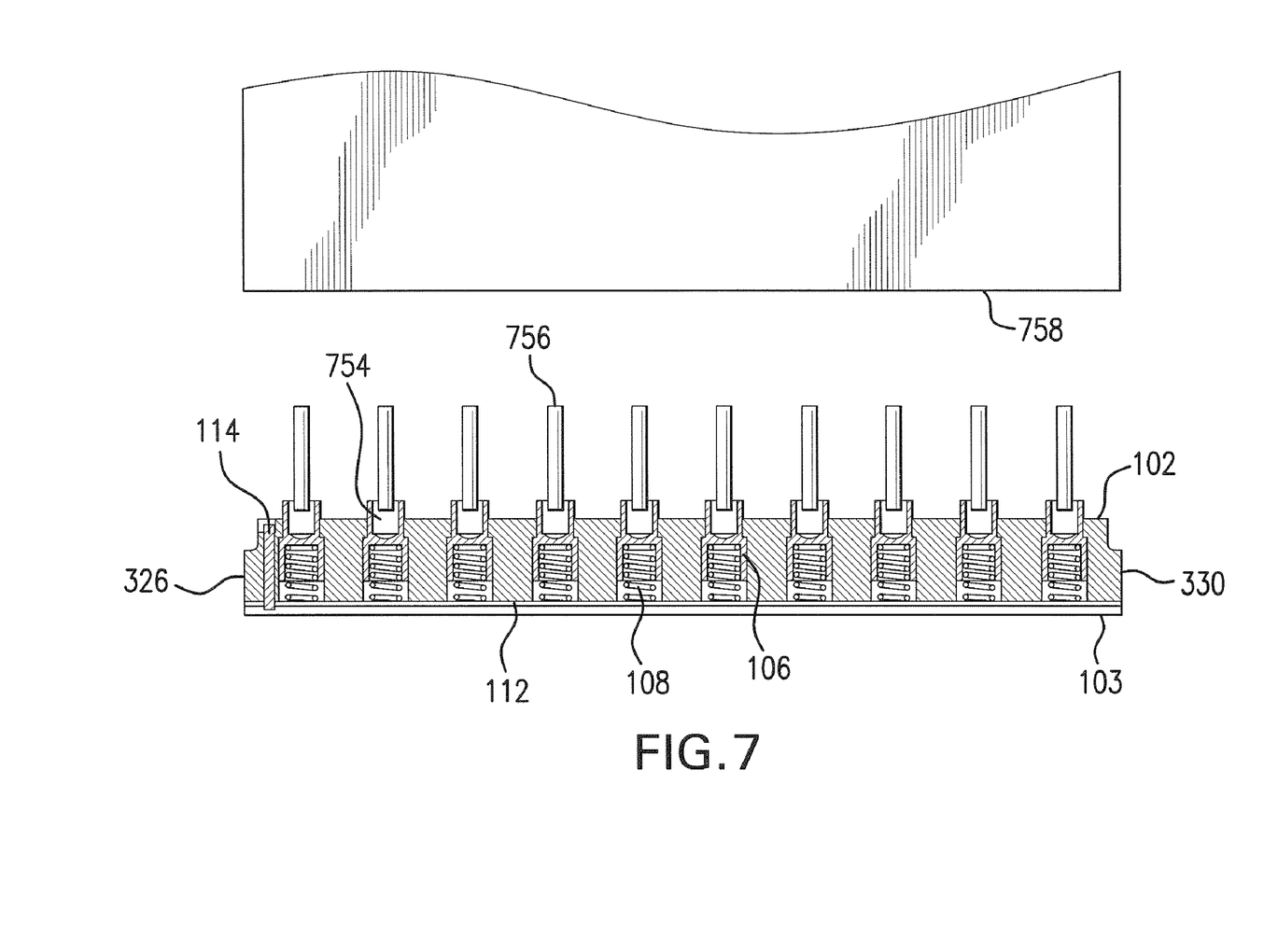
FIG. 7 is a cross sectional view of the work holder with the tablets and handles before attachment.
Figure 8:
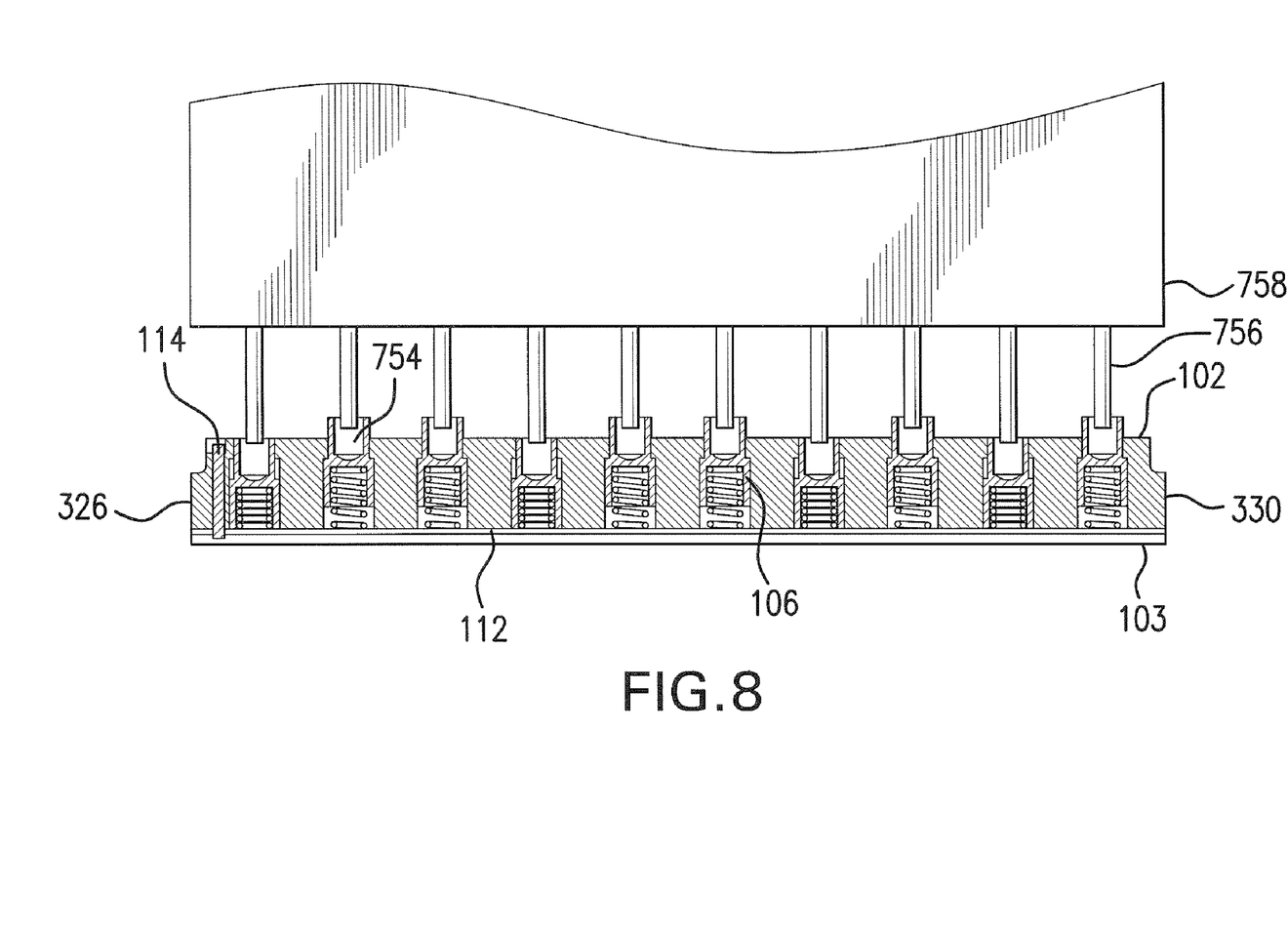
FIG. 8 is a cross sectional view of the work holder with the tablets and handles during attachment.

The method for utilizing the work holder 100 for attaching a handle to a tablet, such as a solid oral dosage form will be described with reference to FIGS. 7 and 8. High frequency mechanical vibrations, such as, for example, ultrasonic vibrations, can be utilized for attaching a handle to a solid oral dosage form. High frequency mechanical vibrations are used to melt materials using friction between the parts in contact, causing a localized melting between at least one of the materials. The parts are then held in contact by pressure until the material cools down and forms a bond at a joint interface. Creation of the bond increases the attachment of the solid oral dosage form to the handle, thus reducing the probability that the solid oral dosage form will become detached from the handle.

A plurality of tablets 754 and handles 756 are placed in upper cavities 220 of bullets 106. The tablet portion of a lollipop can include a normal sucker candy or a solid oral dosage form. The term "solid oral dosage form" refers to a solid object of a size capable of being placed in an oral cavity, the solid object comprising a matrix capable of releasing an active agent. In some embodiments, the matrix can be substantially free of allergens and additives such as synthetic flavorings, dyes, preservatives, and alcohols.

The solid oral dosage form can be comprised of various materials, as long as at least one of the materials in the dosage form is meltable. As used herein, "meltable" refers to the physical property of the material such that the material can undergo a physical change, e.g., from a solid state to a liquid state, with a change in temperature. In some embodiments, the meltable material can melt at a temperature of about 25° C. to about 200° C., or about 40° C. to about 180° C. In some embodiments, the meltable material can melt at an elevated temperature of from about 50° C. to about 200° C., or about 75° C. to about 150° C. In some embodiments, the meltable material undergoes a physical changes at a temperature that is at least about 25° C. above room temperature. "Non-meltable" means all pharmaceutically acceptable materials having a melting point above 220° C. and those materials that decompose instead of melting. In some embodiments, the meltable material will resolidify when the compound is returned to a temperature below the temperature at which the melting occurred. As used herein, a solid oral dosage form comprising a meltable material is a solid or semisolid at room temperature (about 25° C.). These meltable materials can be further classified as either hydrophilic or hydrophobic.

Suitable meltable hydrophilic materials for use in the present invention include povidone, polyethylene glycol, and mixtures thereof. Suitable meltable hydrophobic materials for use in the present invention include magnesium stearate, calcium stearate, aluminum stearate, hydrogenated vegetable oil, and mixtures thereof.

In some embodiments, the amount of meltable material, either hydrophilic, hydrophobic, or a mixture thereof, present in the oral dosage form is about 1% to about 95% of the weight of the solid oral dosage form. In some embodiments, the meltable material present in the oral dosage form is about 1% to about 75%, or about 1% to about 55%, or about 1% to about 35%, or about 1% to about 15% of the weight of the solid oral dosage form. In some embodiments, the meltable material is about 15% of the weight of the solid oral dosage form. In some embodiments, the meltable material present in the oral dosage form is about 5% to about 95%, or about 10% to about 80%, or about 15% to about 60%, or about 15% to about 40% of the weight of the solid oral dosage form.

In some embodiments, the solid oral dosage form comprises a carbohydrate-free matrix. In some embodiments, the carbohydrate-free matrix is povidone. In some embodiments, the carbohydrate-free matrix comprises an artificial sweetener. In some embodiments, the solid oral dosage form is a "sugar-free solid oral dosage form" or "carbohydrate-free solid oral dosage form." The terms "sugar-free solid oral dosage form" or "carbohydrate-free solid oral dosage form" refer to dosage forms that are substantially free of carbohydrates. Substantially free of carbohydrates means that the dosage form contains less than about 5.0% by weight of carbohydrate. In some embodiments, substantially free of carbohydrates means the dosage form contains less than about 3% by weight, or less than about 2% by weight, or even less than about 1% by weight of carbohydrate. In some embodiments, the term substantially free of carbohydrates means that the dosage form contains no carbohydrates. In some embodiments, the dosage form contains less than 0.5 g of carbohydrates per dosage form. In some embodiments, the matrix comprises a carbohydrate-containing matrix. As used herein, the term "carbohydrate" refers to compounds that are polyhydroxy aldehydes or ketones, or substances that yield such compounds on hydrolysis. Many, but not all, carbohydrates have the empirical formula $(CH_2O)_n$. Some carbohydrates can also contain nitrogen, phosphorous, or sulfur as described in *Lehninger: Principles of Biochemistry*, W. H. Freeman and Company, $4^{th}$ ed. (2005), herein incorporated by reference. The major classes of carbohydrates include monosaccharides, disaccharides, oligosaccharides, and polysaccharides. All four classes are considered by the present invention as carbohydrates. For example, in some embodiments the solid oral dosage form comprising a carbohydrate matrix can comprise starch, sucrose, fructose, or combinations thereof.

In some embodiments, the solid oral dosage form can comprise an excipient. In some embodiments, the excipient can be, but is not limited to, an absorbent, buffering agent, colorant, flavorant, solvent, coating agent, direct compression agent, disintegrant, glidant, lubricant, opaquant, suspending agent, sweetening agent, anti-adherent, binder, preservative, or combinations thereof.

The term "attached" refers to the fastening of the handle to the tablet, such as a solid oral dosage form. The attachment bond strength can vary. In some embodiments, about 1 pound to about 70 pounds of force is required to detach the handle from the solid oral dosage form. In some embodiments, about 5 pounds to about 70 pounds of force is required to detach the handle from the solid oral dosage form. The attachment bond strength is determined by a "pull force tester, such as a Chatillon TCD 201 MF Series Tester stand and Chatillon DFA-50 digital force gauge (Chatillon Force Measurement Systems, Largo, Fla.).

The term "handle" refers to any feature of the device, distinct in composition from the solid oral dosage form, which protrudes from the solid oral dosage form which allows an individual to insert and remove the solid oral dosage form from an oral cavity. In some embodiments, the term "handle" refers to a means for removing the solid oral dosage form from an oral cavity. In some embodiments, the handle is rigid, e.g., a stick or rod. In some embodiments, the handle is flaccid, e.g., a string or cord. The handle can vary in shape. In some embodiments, the handle is relatively straight. In some embodiments, the handle is ring-shaped. In some embodiments, the handle is malleable, and can be bent or altered to achieve a desired shape. The handle can vary in size. In some embodiments, when the solid dosage form is placed inside a subject's oral cavity, the handle is large enough to protrude outside the subject's mouth. In some embodiments, when the solid dosage form is placed inside a subject's oral cavity, the handle is small enough to reside in the oral cavity when the mouth is closed.

The term "joint interface" refers to the area of contact between the handle and the solid oral dosage form. In some embodiments, the joint interface has an area of about 0.01 cm² to about 10 cm². In some embodiments, the joint interface has an area of about 0.1 cm² to about 1 cm².

Apparatuses that generate high frequency mechanical vibrations are known to those in the art. For example, in some embodiments the apparatus can comprise a Branson 2000 AED Actuator and a Branson 2000 D power supply (Branson, Danbury, Conn.). An apparatus for producing and transferring high frequency mechanical vibrations generally contains four parts: a power supply, a converter, an amplitude modifying device (commonly called a booster) and an acoustic tool known as the horn (or sonotrode). In some embodiments, high frequency mechanical vibrations are created by using a solid-state power supply to change 50/60 Hz electrical current into about 15, 20, 30, or 40 kHz electrical energy. This high frequency electrical energy is supplied to a converter, which transforms the electrical energy to mechanical motion at high frequencies. The mechanical motion, i.e., vibratory energy, is then transmitted through an amplitude-modifying booster to the horn. The horn transfers this vibratory energy directly to the parts being assembled.

Once tablets 754 and handles 756 have been placed in upper cavities 220 of bullets 106, a horn 758 of a mechanical vibration apparatus is lowered to contact handles 756. Horn 758 can comprise various materials. In some examples, the horn material comprises aluminum or titanium. Springs 108, one of which is located each of in lower cavities 222 of bullets 106, contact plate 112 and top flat surface 650 of lower cavity 222, to allow for consistent welding of handles 756 to tablets 754. It is often the case that some of handles 756 are not fully inserted into tablets 754, which results in some of handles 756 being closer to horn 758 than others prior to lowering horn 758 into contact with handles 756. As illustrated in FIG. 8, the spring action of springs 108 permits relative movement of bullets 106 with respect to each other so that horn 758 will come into contact with each handle 756 to ensure consistent welding and attachment of handles 756 to tablets 754 and allows handles 756 that were initially closer to horn 758 to be lowered by compressing the spring 108 associated with the bullet 106 in which the handle 756 is located. The spring action, therefore provides consistent pressure to each of handles 756 and prevents some of handles 756 from receiving too much pressure from horn 758, which would lead to cracking of tablets 754.

The horn 758 transmits the mechanical vibrations and applies pressure to increase contact between the handles 756 and the tablets 754 during application of the high frequency mechanical vibrations. In some embodiments, the pressure is about 1 psi to about 100 psi, or about 2 psi or about 50 psi. In some embodiments, the pressure is about 10 psi to about 20 psi.

In some embodiments, an automated post-welding inspection is performed to ensure adequate welding between each pair of tablet 754 and handle 756. Hole 334 in tooling pallet 101 houses a RFID tag, which receives signals containing information whether the weld between each pair of tablet 754 and handle 756 has passed inspection. If a weld has not passed inspection, then the RFID tag sends signals to a removal device, for example, an unloading robot arm, containing the information for each bullet 104 that contains a defective weld between a tablet 754 and a handle 756 so that the defective lollipop may be removed. After removal of the defective lollipops, the remaining lollipops are processed for packaging.

Various frequencies can be used in the present invention. The term "high frequency" refers to frequencies above 1 kHz. In some embodiments, high frequency refers to frequencies of about 1 kHz to about 10 MHz. In some embodiments, the high frequency mechanical vibrations have a frequency of about 5 kHz to about 100 kHz. In some embodiments, the high frequency mechanical vibrations have a frequency of about 15 kHz to about 40 kHz. In some embodiments, the high frequency mechanical vibrations are ultrasonic vibrations. The term "ultrasonic" refers to frequencies of sound energy higher than the upper limit of the human hearing range, about 20 kHz. In some embodiments, the ultrasonic frequencies are about 20 kHz to about 1 MHz. In some embodiments, the ultrasonic frequencies are about 20 kHz to about 500 kHz, about 20 kHz to about 200 kHz, or about 20 kHz to about 50 kHz.

Various types of vibrational energy can be used. In some embodiments the high frequency vibrations are linear vibrations. When using linear vibrations, frictional heat is generated by moving one part against the other under pressure through a linear displacement plane of the joint or amplitude. When a molten state is reached at the joint interface, vibration is stopped. Clamping pressure is maintained briefly while the molten material solidifies to form a bond. In some embodiments, the high frequency vibrations are orbital vibrations. Orbital vibrations use an electromagnetic drive to create a relative circular motion between the solid oral dosage form and the handle. This constant velocity motion generates heat, which raises the material temperature at the joint to its melting point. The motion is terminated after sufficient material is melted. The melted material then solidifies and forms a permanent bond.

Various oscillation amplitudes can be used in the present invention. In some embodiments, the high frequency mechanical vibrations have an oscillation amplitude of 1 μm to 1 cm. In some embodiments, the high frequency mechanical vibrations have an oscillation amplitude of 5 μm to 300 μm. In some embodiments, the high frequency mechanical vibrations have an oscillation amplitude of 10 μm to 100 μm.

The length of time used to apply the high frequency vibrations is dependent on several factors. These factors can include, but are not limited to, the composition of both the handle and the solid oral dosage form, the amount of pressure applied to the interface, the size of the joint interface between the handle and the solid oral dosage form, the frequency of the vibration, and the amplitude of the vibration. In some embodiments, the high frequency vibrations are applied for about 1 millisecond to about 30 seconds. In some embodiments, the high frequency vibrations are applied for about 0.1 second to about 10 seconds. In some embodiments, the high frequency vibrations are applied for about 0.1 second to about 5 seconds. In some embodiments, the high frequency vibrations are applied for about 1 second.

By applying high frequency mechanical vibrations to the joint interface, the solid oral dosage form at the joint interface can reach a molten state. The term "molten state" refers to the liquefied physical state of a material caused by heat.

In some embodiments, the solid oral dosage form further comprises an active agent. Various active agents can be used. In some embodiments, the active agent can be, but is not limited to, methohexital, pentobarbital, thiamylal, thiopental, fentanyl, modafinil, alfentanil, sufentanil, lofentanil, carfentanil, naloxone, epam, lorazepam, midazolam, oxazepam, triazolam, droperidol, propanidid, etomidate, propofol, ketamine, diprivan, bretylium, captopril, clonidine, dopamine, enalapril, esmolol, furosemide, isosorbide, labetalol, lidocaine, metolazone, metoprolol, nadolol, nifedipine, nitroglycerin, nitroprusside, propranolol, benzquinamide, meclizine, metoclopramide, prochlorperazine, trimethobenzamide, clotrimazole, nystatin, carbidopa, levodopa, sucralfate, albuterol, amninophylline, beclomethasone, dyphylline, epinephrine, flunisolide, isoetharine, isoproterenol HCl, metaproterenol, oxtriphylline, terbutaline, theophylline, ergotamine, methysergide, propranolol, suloctidil, ergonovine, oxytocin, desmopressin, acetate, lypressin, vasopressin, insulin, beta-endorphin, enkephalins, bradykinin, aniotensin I, gonadotropic hormones, adrenocorticotropic hormone (ACTH), calcitonin, parathyroid hormone, growth hormone, polysaccharides (such as heparin), salts or esters thereof, or combinations thereof. In some embodiments, the active agent is fentanyl or salt thereof, e.g., fentanyl citrate, or combinations thereof. In some embodiments, the active agent is fentanyl.

In the present invention, the handle can comprise various materials. In some embodiments, the handle comprises acetonitrile butadiene styrene, a thermoplastic, a semi-crystalline thermoplastic, an olefin, a thermostat polymer, a thermoplastic rubber, a composite plastic, or a mixture thereof. In some embodiments, the handle comprises a non-plastic material, e.g., a metal. In some embodiments, the handle comprises tubing.

The solid oral dosage form can be manufactured by different methods. In some embodiments, the active agent is added to a molten candy mass. The resultant mixture can then be thoroughly mixed to ensure proper distribution of the active agent within the molten candy mass. The mixture is then poured while still molten and allowed to solidify into a semi-solid mass. In some embodiments, the hot candy mass can be poured into molds, the size and shape of which can be determined as desired.

The tablet, such as a solid oral dosage form can also be made by direct compression, injection molding, freeze-drying or other solid processing techniques. In some embodiments, the solid oral dosage form is a compressed dosage form. In some embodiments, the handle is in contact with the solid oral dosage form when the solid oral dosage form is being formed. For example, in a compressed dosage form, the handle can be present during the compression of solid oral dosage form. Thus, the handle is placed in a mold, the solid oral dosage form is formed around it. Alternatively, the solid oral dosage form can be formed in the absence of a handle, and then the handle can be placed in contact with the solid oral dosage later. In some embodiments, the solid oral dosage form is formed with a cavity. In some embodiments, a portion of the handle can fit inside the cavity.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

What is claimed is:

1. A method for attaching a handle to a tablet to form a lollipop, the method comprising:
   providing a work holder comprising:
      a tooling pallet having a first surface, a second surface, and a plurality of openings in the first surface;
      a plurality of bullets, wherein each bullet has a first cavity, and wherein each of the plurality of bullets is inserted into one of the plurality of openings in the tooling pallet; and
      a plurality of springs, wherein each of the plurality of springs is located in one of the plurality of openings in the tooling pallet between one of the plurality of bullets and a surface;
   placing a tablet in each of the first cavities of the plurality of bullets;
   placing a handle in contact with each tablet so that a longitudinal axis of each handle is parallel to a longitudinal axis of the spring associated with the bullet holding the tablet, wherein an area of contact between each handle and each tablet forms a joint interface;
   applying high frequency mechanical vibrations to the joint interfaces until each tablet at each joint interface reaches a molten state; and
   cooling the joint interfaces in a molten state to allow solidification, thereby attaching a handle to each tablet.

2. The method of claim 1, wherein each tablet is a solid oral dosage form.

3. The method of claim 2, wherein the high frequency mechanical vibrations are generated by a horn.

4. The method of claim 3, wherein the horn moves towards work holder to contact each of the handles, wherein each of the plurality of springs allows for movement of each of the plurality of bullets independent of the other bullets.

5. The method of claim 4, wherein the independent movement of each of the plurality of bullets from the other bullets prevents the solid dosage form in each of the plurality of bullets from being crushed through the exertion of too much pressure by the horn.

6. The method of claim 4, wherein the independent movement of each of the plurality of bullets from the other bullets compensates for differences in a height of each of the handles to ensure each handle is in contact with the horn by compressing each spring until the horn is in contact with each handle.

7. The method of claim 2, wherein the solid oral dosage form comprises an active agent.

8. The method of claim 7, wherein the active agent is fentanyl, fentanyl citrate, or combinations thereof.

9. The method of claim 3, wherein the horn applies pressure to the handles during application of the high frequency mechanical vibrations in an amount from about 1 psi to about 100 psi.

10. The method of claim 1, wherein the joint interface has an area of about 0.01 $cm^2$ to about 10 $cm^2$.

11. The method of claim 1, wherein the high frequency mechanical vibrations are ultrasonic vibrations.

12. The method of claim 11, wherein the ultrasonic vibrations are linear vibrations or orbital vibrations.

13. The method of claim 1, wherein the high frequency mechanical vibrations have a frequency of about 5 kHz to about 100 kHz.

14. The method of claim 1, wherein the high frequency mechanical vibrations have a frequency of about 15 kHz to about 40 kHz.

15. The method of claim 1, wherein the high frequency mechanical vibrations have an oscillation amplitude of about 5 μm to about 300 μm.

16. The method of claim 1, wherein the high frequency mechanical vibrations have an oscillation amplitude of about 10 μm to about 100 μm.

17. The method of claim 1, wherein the handle comprises acetonitrile butadiene styrene, a thermoplastic, a semi-crystalline thermoplastic, a thermostat polymer, an olefin, a thermoplastic rubber, a metal, a composite plastic or a mixture thereof.

18. The method of claim 1, wherein the handle is rigid.

19. The method of claim 1, wherein the high frequency mechanical vibrations are applied for about 0.1 seconds to about 10 seconds.

* * * * *